United States Patent
Sullivan et al.

(10) Patent No.: US 8,189,975 B2
(45) Date of Patent: May 29, 2012

(54) FIBER SPECTROSCOPIC PROBE MOUNTABLE ON A MICROSCOPE

(75) Inventors: Ryan Edward Sullivan, Yardley, PA (US); Qingxiong Li, Newark, DE (US); Xin Jack Zhou, Hockessin, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 289 days.

(21) Appl. No.: 12/573,278

(22) Filed: Oct. 5, 2009

(65) Prior Publication Data

US 2011/0081110 A1   Apr. 7, 2011

(51) Int. Cl.
*G02B 6/06*   (2006.01)

(52) U.S. Cl. ............ 385/116; 385/31; 385/33; 356/301; 436/46; 436/514; 250/584

(58) Field of Classification Search ............... 385/31, 385/33, 116; 356/301; 436/46, 514
See application file for complete search history.

(56) References Cited

U.S. PATENT DOCUMENTS

| | | | |
|---|---|---|---|
| 5,194,912 A * | 3/1993 | Batchelder et al. | 356/301 |
| 7,102,746 B2 | 9/2006 | Zhao | |
| 7,403,281 B2 | 7/2008 | Carron et al. | |
| 2005/0128476 A1* | 6/2005 | Zhao | 356/301 |
| 2011/0081111 A1* | 4/2011 | Li et al. | 385/33 |

* cited by examiner

*Primary Examiner* — Jack Berman
*Assistant Examiner* — Meenakshi Sahu

(57) ABSTRACT

A fiber spectroscopic probe that can be mounted directly above the objective lens of a standard microscope to add a spectroscopic function to the microscope. The fiber spectroscopic probe only consists of a minimum number of optical components and is compact enough to induce minimum alteration to the optical path of the microscope.

7 Claims, 2 Drawing Sheets

US 8,189,975 B2

FIBER SPECTROSCOPIC PROBE MOUNTABLE ON A MICROSCOPE

FIELD OF THE INVENTION

This invention generally relates to a fiber spectroscopic probe, and more specifically to a fiber spectroscopic probe mountable on a microscope.

BACKGROUND

Raman microscopy is a useful technique that permits non-destructive, spatially resolved measurements within the samples. Conventional Raman microscopes such as those disclosed in U.S. Pat. No. 5,194,912 to Batchelder et al. suffer from bulky sizes, which limits them only to laboratory usages. Recently, with the development of diode lasers as the excitation light source, Raman spectrometers were made as compact attachments that can be mounted onto a standard microscope to convert it into a Raman microscope. Some exemplary apparatus can be found in U.S. Pat. No. 7,102,746 to Zhao and U.S. Pat. No. 7,403,281 to Carron et al., which are hereby incorporated herein as references. Yet the large number of optical components in a Raman spectrometer still places a lower limit on its physical size. As a result, the incorporation of the Raman spectrometer inevitably alters the optical path length of the microscope. Certain modifications have to be made to the microscope to accommodate the Raman spectrometer, which may affect the microscope's normal function.

There thus exists a need for an improved spectroscopic accessory that can be mounted onto a standard microscope to add a spectroscopic function to the microscope and in the meantime induces minimum alteration to the optical path of the microscope.

SUMMARY OF THE INVENTION

It is the overall goal of the present invention to solve the above mentioned problems and provide a fiber spectroscopic probe that can be mounted directly above the objective lens of a standard microscope to add a spectroscopic function to the microscope. The fiber spectroscopic probe only consists of a minimum number of optical components and is compact enough to induce minimum alteration to the optical path of the microscope.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
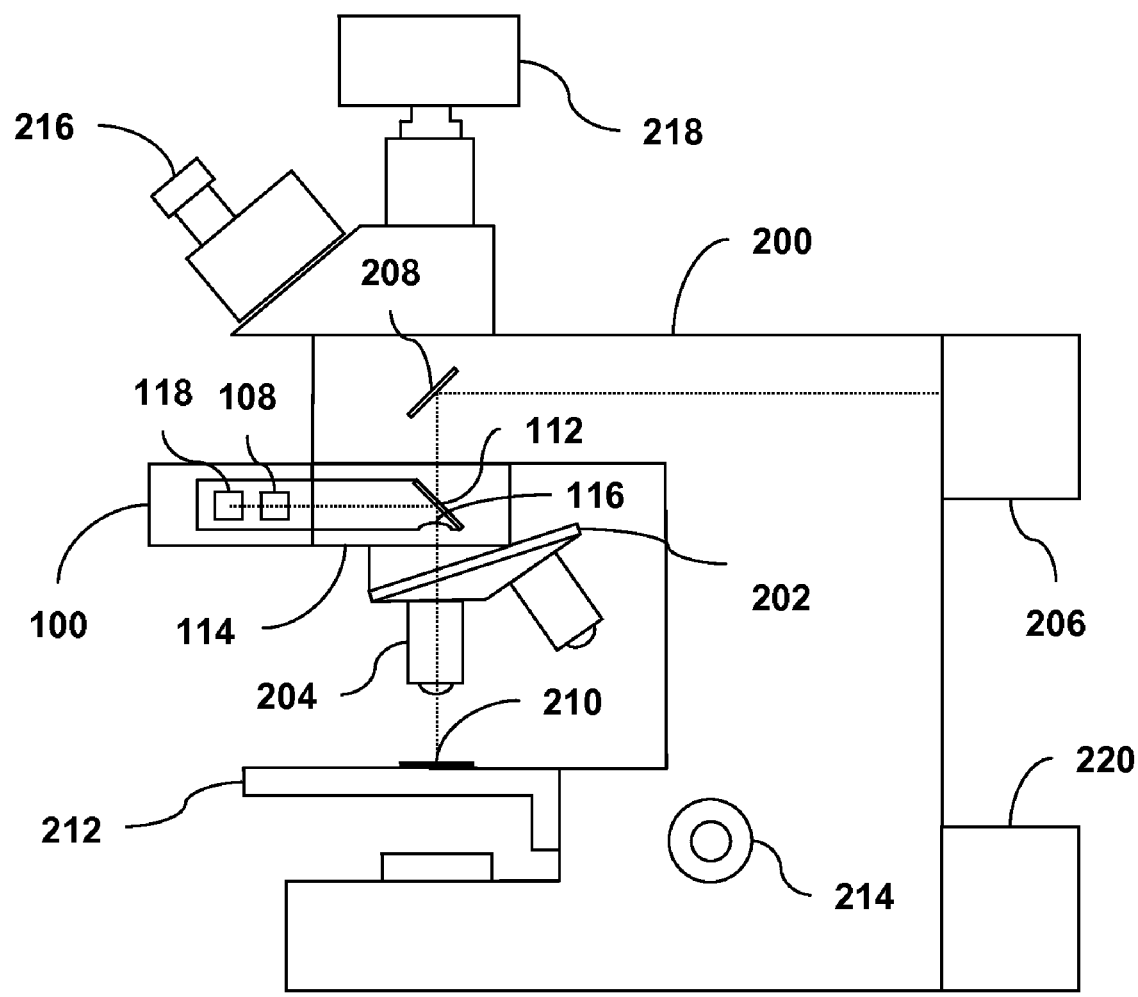
FIG. 1 is a schematic side view of a fiber spectroscopic probe mounted on a microscope.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a fiber spectroscopic probe mountable on a microscope. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 2:
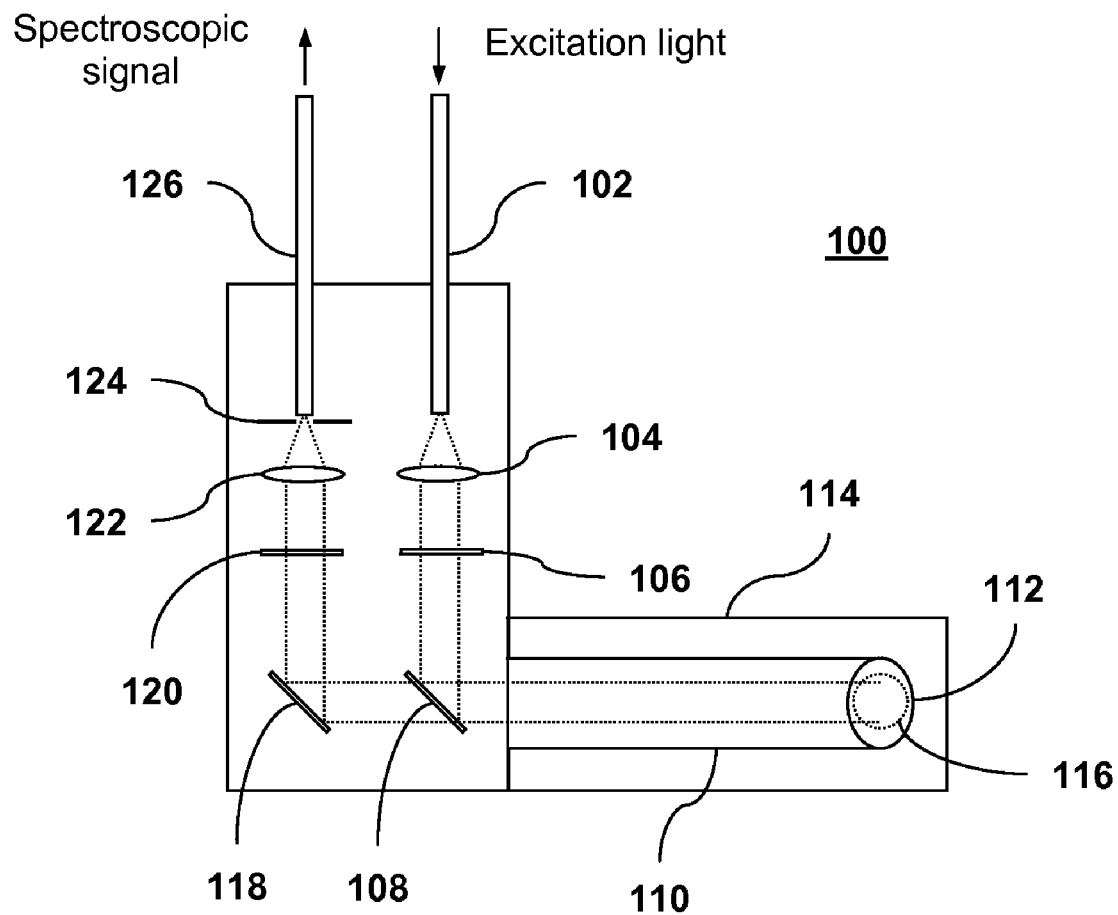
FIG. 2 is a schematic top view of the fiber spectroscopic probe of FIG. 1.

FIG. 1 and FIG. 2 show a schematic side view and a schematic top view of an exemplary fiber spectroscopic probe 100, respectively. In this exemplary embodiment, the fiber spectroscopic probe 100 is a fiber Raman probe, which can be mounted onto a standard microscope 200 to convert it into a Raman microscope.

Referring to FIG. 1, the microscope 200 is a standard light microscope comprising the following components: an epi-illumination light source 206 and a trans-illumination light source 220 for providing illumination, a stage 212 for holding the sample 210, a nosepiece 202 and a plurality of objective lenses 204 for collecting the reflected or transmitted light from the sample, as well as an eyepiece 216 and a camera 218 as the viewing device. The epi-illumination light produced by the light source 206 is reflected by a beam splitter 208 (preferably a half-silvered mirror) into the main optical path of the microscope. The focus of the microscope can be adjusted though a knob 214.

Referring to FIG. 1 and FIG. 2, the fiber Raman probe 100 comprises an input optical fiber 102 for delivering excitation light from a laser light source (not shown). The laser light from the input optical fiber 102 is collimated by an optical lens 104 and transmits through a band-pass optical filter 106 to remove the out-of-band background noise. The filtered laser light is then reflected by a dichroic beam splitter 108 to be directed toward an output tube 110. The output tube 110 is enclosed in an adapter member 114 to be mounted onto the microscope 200 in a position directly on top of the nosepiece 202 and the objective lens 204. Another dichroic beam splitter 112 mounted at the end of the output tube 110 is used to reflect the laser light down through a hole 116 on the tube to the objective lens 204 to be focused onto the sample 210. Here the laser light shares the same optical path as the illumination light of the microscope. The laser light excites a Raman scattered light (a spectroscopic signal) from the sample 210, which is collected by the objective lens 204 and then reflected by the dichroic beam splitter 112 into the output tube 110. The Raman scattered light transmits through the dichroic beam splitter 108 to be reflected by a mirror 118 and directed toward a long-pass optical filter 120 and an optical lens 122. The long-pass optical filter 120 acts as a Rayleigh rejection filter to remove the Rayleigh scattered light from the Raman scattered light. The optical lens 122 then focuses the Raman scattered light into an output optical fiber 126 to be transmitted to a spectrometer device (not shown) for spectrum analysis. In this exemplary embodiment, the laser light source is preferably a diode laser with its output wavelength in the near infrared (NIR) region. The dichroic beam splitter 112 is transmissive to the visible illumination light and reflective to the NIR laser light and the Raman scattered light. The dichroic beam splitter 108 has a cut-off wavelength near the laser wavelength to reflect the laser light and in the meantime transmit the Raman scattered light at longer wavelengths.

The output optical fiber 126 of the fiber Raman probe 100 has a limited optical aperture of less than a few hundred microns. Thus most of the out-of-focus light from the sample will be rejected by the output optical fiber 126. This adds a confocal feature to the constructed Raman microscope and allows it to examine a series of sections of the sample at different depths. A spatial pinhole 124 (either fixed or adjustable) can be inserted in front of the output optical fiber 126 to further enhance this spatial filtering effect.

The fiber Raman probe 100 contains only a minimum number of optical components. As a result, its thickness can be made very small (e.g. <1 cm) so that the incorporation of the fiber Raman probe only induces a minimum alteration to the optical path length of the microscope. This brings in several advantages. First, the fiber Raman probe 100 can be mounted directly above the nosepiece 202 and the objective lens 204 of the microscope, where the light beam exhibits the smallest spot size in the optical path. Thus the Raman scattered light from the sample can be effectively collected by the fiber Raman probe and in the meantime, the reflected (epi-illumination mode) or transmitted (trans-illumination mode) visible light from the sample 210 will not be blocked. Second, the illumination condition of the microscope (such as Kohler illumination in the epi-illumination mode) will not be disturbed by the incorporation of the fiber Raman probe. Third, the fiber Raman probe does not occupy any viewing port of the microscope hence not affecting its normal viewing function.

With some minor modifications to its optical components, the same fiber probe 100 can be used for other spectroscopic applications as well. For example, by replacing the NIR laser light source with an ultraviolet (UV) or visible light source and adjusting the spectral property of the optical components correspondingly, the fiber probe can convert a standard microscope into a fluorescence microscope for examining the fluorescence or phosphorescence property of the samples.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A fiber spectroscopic probe mountable on a standard light microscope, said fiber spectroscopic probe comprising:
   an input optical fiber for delivering excitation light from an external light source;
   an adapter means mountable directly above an objective lens of the microscope for directing said excitation light through said objective lens to a sample to excite a spectroscopic signal and collecting said spectroscopic signal though said objective lens; and
   an output optical fiber for delivering said spectroscopic signal to an external spectrometer device for spectral analysis.

2. The fiber spectroscopic probe of claim 1, wherein said adapter means does not occupy any viewing port of the microscope.

3. The fiber spectroscopic probe of claim 1, wherein said spectroscopic signal is a Raman scattering signal.

4. The fiber spectroscopic probe of claim 1, wherein said spectroscopic signal is a fluorescence signal.

5. The fiber spectroscopic probe of claim 1, wherein said adapter means comprises a beam-splitting member.

6. The fiber spectroscopic probe of claim 5, wherein said beam-splitting member has a wavelength-dependent transmissive/reflective property.

7. The fiber spectroscopic probe of claim 1, further comprising a spatial pinhole before said output optical fiber.

* * * * *